United States Patent [19]

Harvill et al.

[11] Patent Number: 5,619,324
[45] Date of Patent: Apr. 8, 1997

[54] METHOD FOR MEASURING PARTICLE SIZE IN THE PRESENCE OF MULTIPLE SCATTERING

[75] Inventors: Thomas L. Harvill, Walnut Creek; Donald J. Holve, Danville, both of Calif.

[73] Assignee: Insitec Measurement Systems, San Ramon, Calif.

[21] Appl. No.: 581,681

[22] Filed: Dec. 29, 1995

[51] Int. Cl.⁶ .................................................. G01N 15/02
[52] U.S. Cl. ................................................................ 356/336
[58] Field of Search ................................... 356/336, 337

Primary Examiner—Frank Gonzalez
Assistant Examiner—Amanda Merlino
Attorney, Agent, or Firm—Skjerven, Morrill, MacPherson, Franklin & Friel; Edward C. Kwok

[57] ABSTRACT

A method applicable to an ensemble laser diffraction (ELD) instrument computes a particle size distribution in real time after correction for the multiple scattering phenomena. In one embodiment, a numerical method, similar to the Newton's method, is provided to iteratively calculate the single scattering mode. The present method is hence suitable for use, with high accuracy, in real time controlling and monitoring applications.

8 Claims, 8 Drawing Sheets

Microfiche Appendix Included
(1 Microfiche, 39 Pages)

METHOD FOR MEASURING PARTICLE SIZE IN THE PRESENCE OF MULTIPLE SCATTERING

CROSS REFERENCE TO MICROFICHE APPENDIX

Appendix A, which is a part of the present disclosure, is a microfiche appendix consisting of 1 sheet of microfiche having a total of 39 frames. Microfiche Appendix A is a listing of computer programs and related data in one embodiment of this invention. This listing of computer programs contains material which is subject to copyright protection. The copyright owner has no objection to the facsimile reproduction by anyone of the patent document or the present disclosure, as it appears in the Patent and Trademark Office patent files or records, but otherwise reserves all copyright rights whatsoever.

BACKGROUND OF THE INVENTION

1. Field of the Invention

This invention relates to measurement of particle size distributions via light scattering.

2. Discussion of the Related Art

One class of laser particle measurement instruments, commonly referred to as Ensemble Laser Diffraction (ELD) instruments, use a laser beam to illuminate particles in a measurement volume and an array of sensors to detect the intensities of light scattered from the laser beam by the particles at various scattering angles. The particle size distribution is then calculated using a light scattering function calculated from either Mie theory or Fraunhofer diffraction theory. However, the light scattering function is predicted for a single scattering mode or signature. In applications with moderate-high particulate loading, however, the intensities detected result from multiple scattering events. In order to accurately compute the particle size distribution, the effects of multiple scattering must be taken into account.

Multiple scattering effects have been modeled in (i) "Modeling of Multiple Scattering Effects in Fraunhofer Diffraction Particle Size Analysis" by E. D. Hirleman, *Particle Characterization* 5, 57–65 (1988), and (ii) "A General Solution to the Inverse Near-forward Scattering Particle Sizing Problem in Multiple Scattering Environments: Theory" by E. D. Hirleman, *Proceeding of the 2nd International Congress on Optical Particle Sizing*, Mar. 5–8, 1990, pp. 159–168. However, while these articles set forth a general model for characterizing the phenomenon of multiple scattering, they do not provide a method for deriving the single scattering signature without assuming, a priori, the particle size distribution. Such methods are impractical for use in an industrial application, such as one which uses the particle size distribution to achieve a real-time control function. In the prior art, the multiple scattering effect is ignored, leading to significant error in the computed particle size distribution.

SUMMARY OF THE INVENTION

According to the present invention, in an ensemble laser diffraction (ELD) instrument, a method is provided to assist the computation of a particle size distribution. Unlike the methods of the prior art, the method of the present invention makes no a priori assumption regarding the particle size distribution, estimating the particle size distribution only from the known optical geometry and the measured scattering signature.

In the method of the present invention, a single scattering signature $S_1$ is first computed to be used in deriving such particle size distribution. This single scattering signature is arrived at by correcting a measured multiple scattering signature $S_m$ for the multiple scattering phenomenon.

The method of the present invention includes the steps of: (i) measuring a scattering signature $S_m$; (ii) assigning an initial value as a current value for a single scattering signature $S_1$; and (iii) using the current value for the single scattering signature $S_1$, iteratively performing, until a predetermined convergence criterion is met, the steps of:

(a) computing a current value of a scattering redistribution function H using the current value of the single scattering signature $S_1$;

(b) computing the probabilities of multiple scattering $P_n$, each of the $P_n$'s denoting the probability of exactly n scattering events, n being an integer greater or equal to 1;

(c) computing a predicted multiple scattering signature $S_{mp}$ using the relation:

$$S_{mp} = \sum_{k=1}^{n} P_n H^{n-1} S_1$$

and (d) updating the current value of the single scattering signature $S_1$ using the measured multiple scattering signature $S_m$ and the predicted multiple signature $S_{mp}$.

In one embodiment, the step of computing the predicted multiple signature $S_{mp}$ is carried out iteratively such that each $H^n$ is obtained by a single matrix multiplication step, multiplying $H^{n-1}$, already computed, to H. In that embodiment, the current value of the single scattering signature $S_1$ is updated using the relation:

$$S_1 \leftarrow \left( \frac{S_m}{S_{mp}} \right) S_1$$

Suitable convergence criterion within the scope of the present invention for the iteratively performing step includes (i) a mean square error computed between the predicted multiple scattering signature $S_{mp}$ and the measured multiple scattering signature $S_m$ falling below a predetermined value; (ii) the successive values of such mean square error differing by less than a second predetermined value; and (iii) the number of times the step of iteratively performing is performed exceeding a predetermined value.

Additional efficiency is achieved by restricting the value n according to relative magnitudes of the probabilities $P_n$ and $P_1$.

The present invention allows a converged value of the single scattering signature $S_1$ to be computed in real time using even a readily available personal computer. Consequently, a particle size distribution can be derived in real time. Computing the particle size distribution in real time allows such distribution to be used for real time process monitoring and controlling applications.

The present invention is better understood upon consideration of the detailed description below and the accompanying drawings.

BRIEF DESCRIPTION OF THE DRAWINGS

FIG. 2b is a side view of ELD instrument 200 shown in FIG. 2a.

DETAILED DESCRIPTION OF THE PREFERRED EMBODIMENTS

Figure 1:
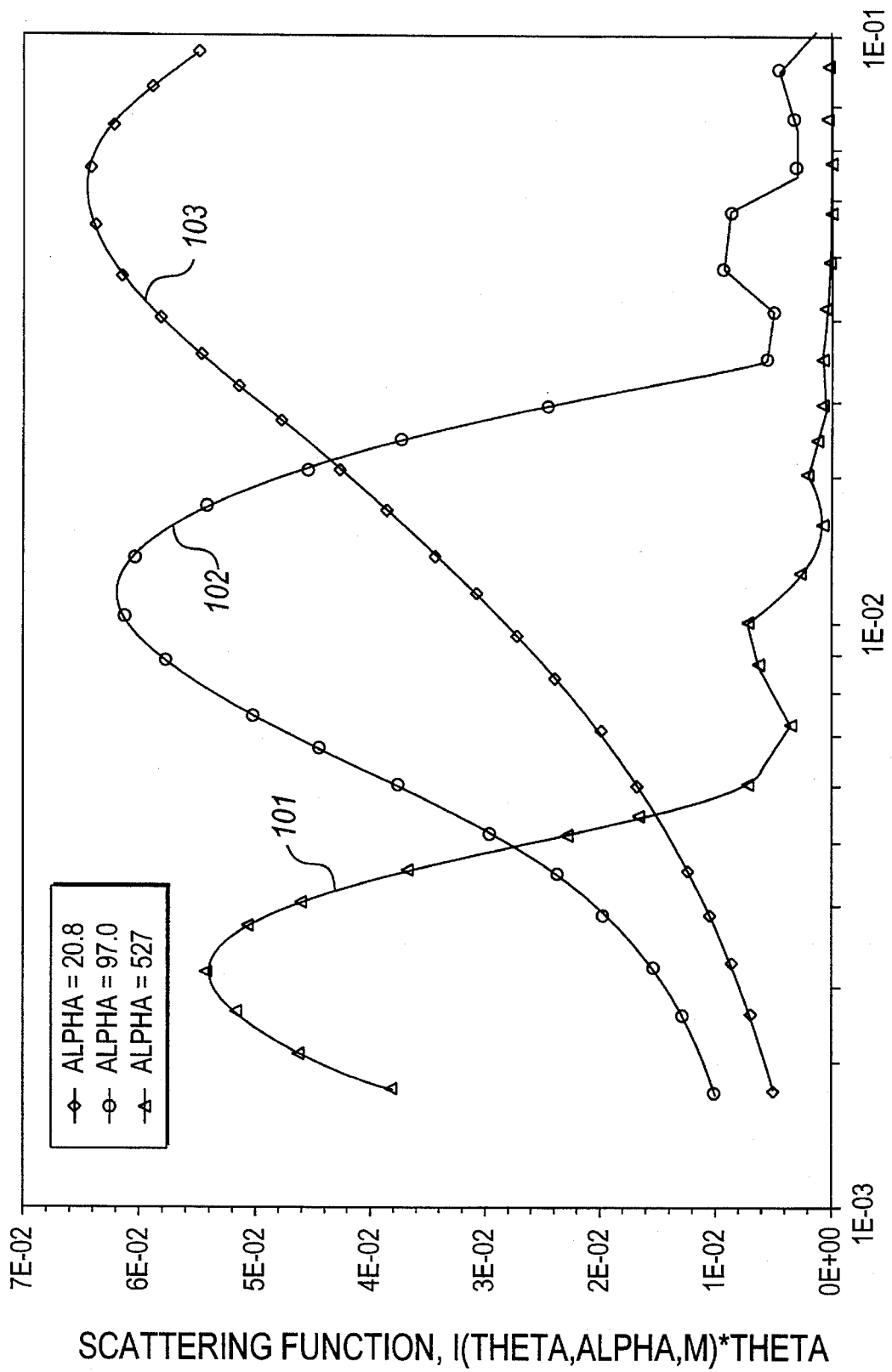
FIG. 1 shows a family of curves representing the light scattering functions for various values of $\alpha$.

The size of a particle can be computed from the scattering angle of light incident on a particle, according to either Mie theory or Fraunhofer diffraction theory. FIG. 1 shows a family of curves 101–103 representing the light scattering functions for various values of "$\alpha$", which is a parameter depending on the particle diameter. $\alpha$, for a given complex refractive index m, is given by:

$$\alpha = \frac{\pi d}{\lambda}$$

where d is the particle diameter; and $\lambda$ is the wavelength of the incident laser beam.

Down to the Rayleigh limit, i.e. where the particle diameter approximates the wavelength of the incident laser beam, the peak intensity of each light scattering function occurs at $$\theta_{max} = \frac{1.357}{\alpha},$$

where $\theta_{max}$ is the scattering angle.

Figure 2A:
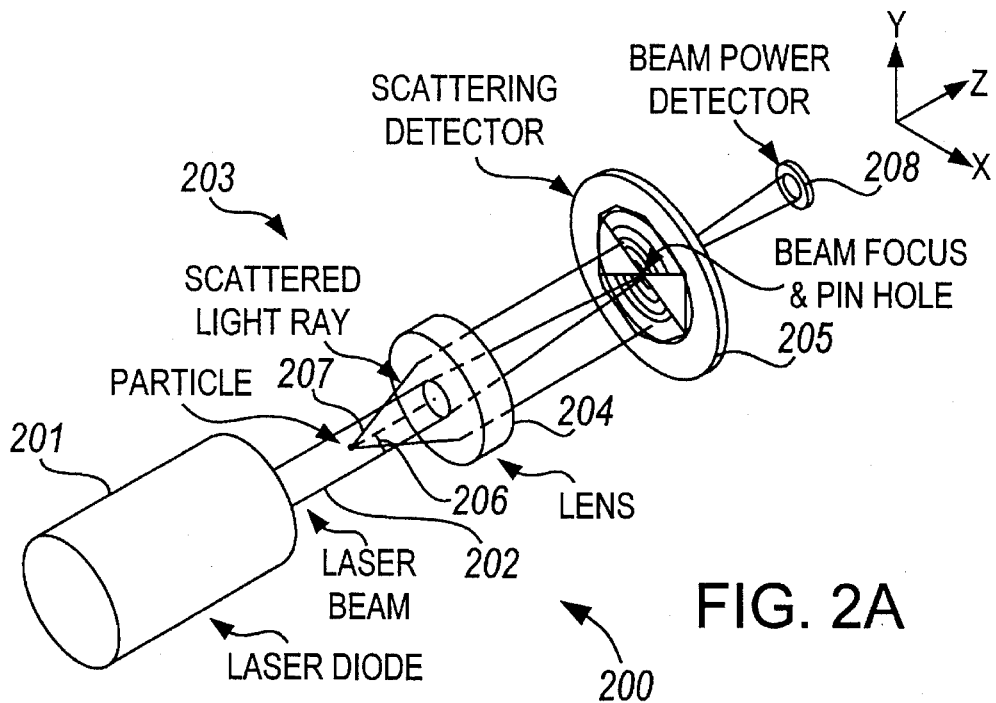
FIG. 2a shows schematically an ensemble laser diffraction (ELD) instrument 200 to which the present invention is applicable.
Figure 2B:
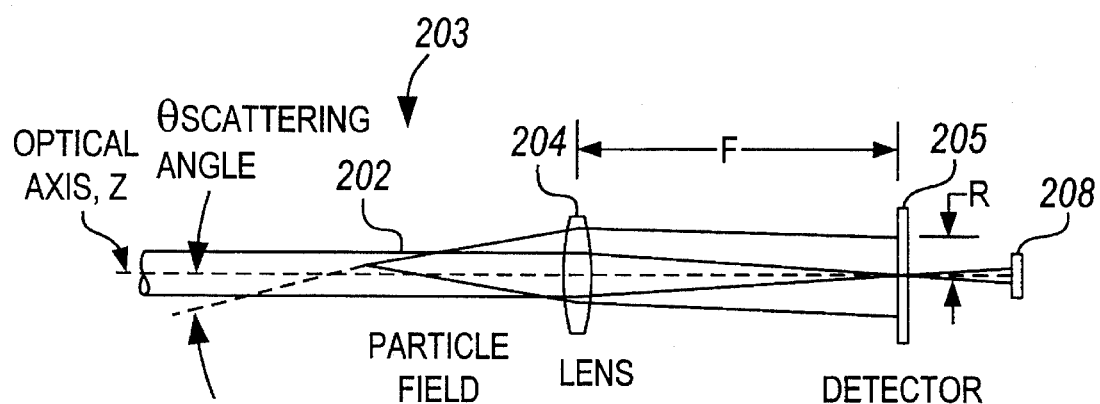

The present invention is applicable to an ensemble laser diffraction instrument, such as ensemble laser diffraction (ELD) instrument 200 shown schematically in FIGS. 2a and 2b. As shown in FIG. 2a, ELD instrument 200 includes a laser source 201, which provides a collimated laser beam 202 incident to a region 203 of particles. The particles in region 203 scatter light from laser beam 202. Lens 204 focuses both the incident beam and the scattered light onto a detector 205. FIG. 2a shows a particle 207 scattering light from laser beam 202 at a scattering angle θ indicated by reference numeral 206. FIG. 2b is a side view of ELD instrument 200. In one embodiment, ELD instrument 200 is provided as an in situ particle monitor mounted on a gas line. In that configuration, particles are carried by a carrier gas flowing in a direction transverse to laser beam 202's direction of propagation. In that embodiment, lens 204 is provided a focal length of 100–500 mm.

Figure 3:
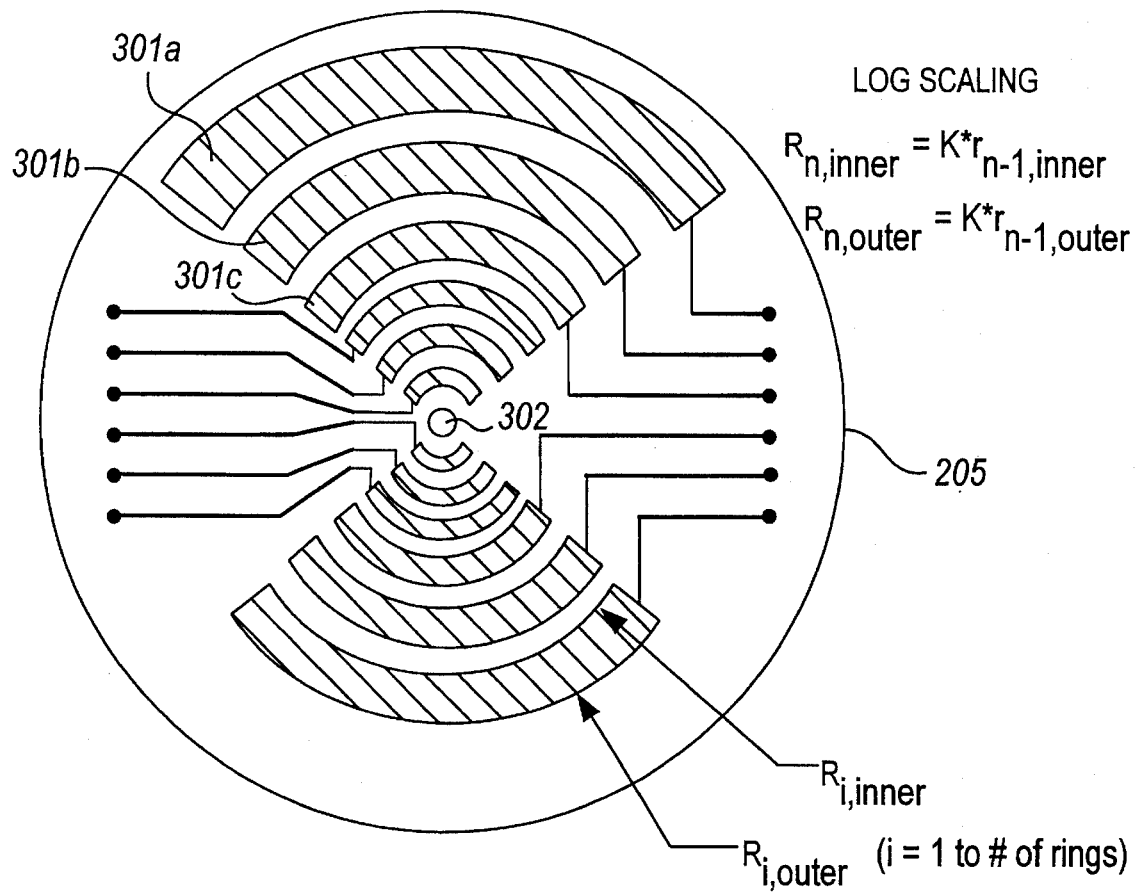
FIG. 3 shows one implementation of detector 205 of ELD instrument 200.

FIG. 3 shows one implementation of detector 205 of ELD instrument 200. As shown in FIG. 3, detector 205 includes a pin hole 302 which allows the transmitted (i.e. unscattered) portion of incident laser beam 202 to pass through detector 205. This transmitted beam is detected by a separate beam power detector 208 located behind detector 205. Detector 205 includes a number of log-scaled annular detector elements ("rings") 301a–301c. Each ring detects light scattered over a range of scattering angles. In one embodiment, the rings are provided at various radii between 150 μm to 16 mm.

In an ELD instrument of the type illustrated by ELD instrument 200 shown in FIG. 2, in the limit when single scattering mode dominates, the scattered light detected $S_1(\theta)$ relates to the particle size distribution V(d) by the equation:

$$S_1(\theta) = C * V(d)$$

where C is a transfer function of the ELD instrument, and the symbol * denotes a convolution. The transfer function C of the ELD instrument is primarily a function of the instrument's optical properties. This equation can be discretized as follows:

$$S(\theta_i) = \sum_j C_{ij} V(d_j)$$

where $\theta_i$ denotes a range i of scattered angles, and $d_j$ denotes a range j of particle sizes ("particle size class"). Of course, to simplify computation, each ring can be made to correspond to one $\theta_i$. The discretized transfer function $C_{ij}$ is seen as:

$$C_{ij} = \sum_{\theta_i} \sum_{d_j} I(\theta_i, d_j) n(d_j) \delta\theta \delta d$$

where (i) $I(\theta_i, d_j)$ is the light scattering function and (ii) $n(d_j)$ is a weighting function based on the number of particles in particle size class $d_j$, such that $V(d_j)$ is normalized to unity for each particle size class $d_j$. Thus, given $S_1(\theta_j)$, the particle size distribution $V(d_j)$ can be derived. $C_{ij}$ is calculated from Mie theory and from knowledge of the optical geometry.

As mentioned above, in all practical applications, since the light intensities detected at detector 205 represents a composite condition which includes multiple scattering, correction to the detected light intensities (i.e. the multiple scattering signature $S_m$) is required to approximate the single scattering mode limit used in determining particle size distribution.

The multiple scattering model is a convolution involving both the probability of the occurrence of a chain of scattering events ($P_n$) and the probability of rescattered light being detected at a defined orientation. $P_n$ is strictly a function of the optical depth b of the measurement volume. Away from the Rayleigh limit, i.e. where particle sizes are much greater than the wavelength of the incident laser beam 202, b is given by:

$$b = \frac{3 C_v L Q}{2 D_{32}}$$

where $C_v$ is the volumetric particle concentration;

Q is the scattering efficiency[1];

L is the length of the measurement volume; and $D_{32}$ is the Sauter Mean Diameter.

[1] Q equals 2 in this embodiment.

The transmission (T) of light through measurement volume is given by:

$$T = e^{-b}$$

The scattering of a photon from the laser beam can be modeled by a Poisson process. Thus $P_n$, i.e. the probability of a photon being scattered exactly n times in its transit through the measurement volume is given by:

$$P_n = \frac{(Qb)^n e^{-b}}{n!}$$

Figure 4:
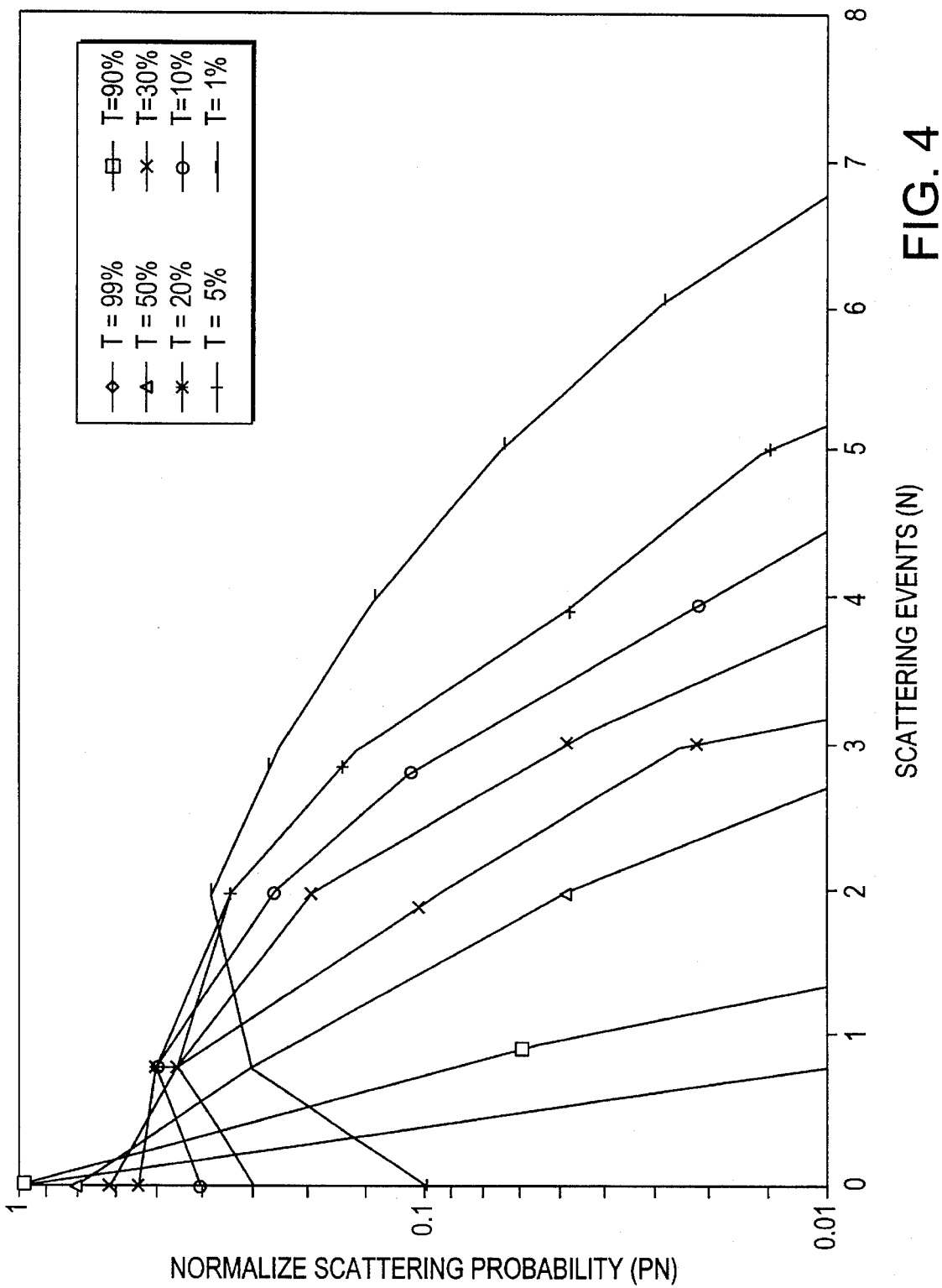
FIG. 4 shows the probabilities of multiple scattering ($P_n$) for different levels of light transmission (T).

The probability of multiple scattering ($P_n$) for different levels of light transmission (T) is shown in FIG. 4. As shown in FIG. 4, $P_n$ increases with lower levels of light transmission. Of course, the probability of transmission ($P_0$), i.e. a photon travels through the measurement volume without a scattering event, is a finite probability.

A scattering redistribution function H ($\theta_{det,i}$, $\theta_{inc,j}$), which is the single scattering transfer function that operates to redirect light incident at angle $\theta_{inc,j}$ to angle $\theta_{der,i}$. Because of the discretization discussed above, the function H can be provided to correspond to the single scattering transfer function that light originally incident at ring j is redirected to ring i. Thus, H can be defined as:

$$H(\theta_{det,i}, \theta_{inc,j}) = \sum_k h(\theta_{det,i},\theta_{inc,j},\theta_{scat,k}) P_{scat}(\theta_{scat,k})$$

where h is a scattering redistribution kernel function, defined below; and $P_{scat,k}$ is the probability of light scattered exactly once at angle $\theta_{scat,k}$.

Figure 5A:
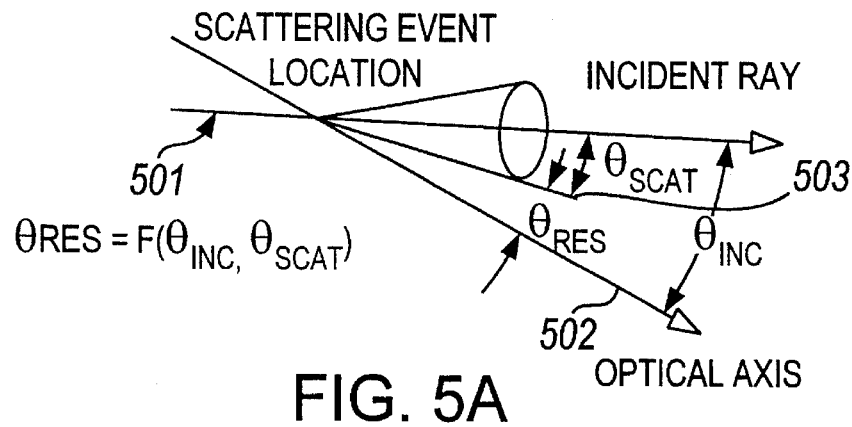
FIG. 5a shows the definitions of various angles in the rescattering geometry.
Figure 5B:
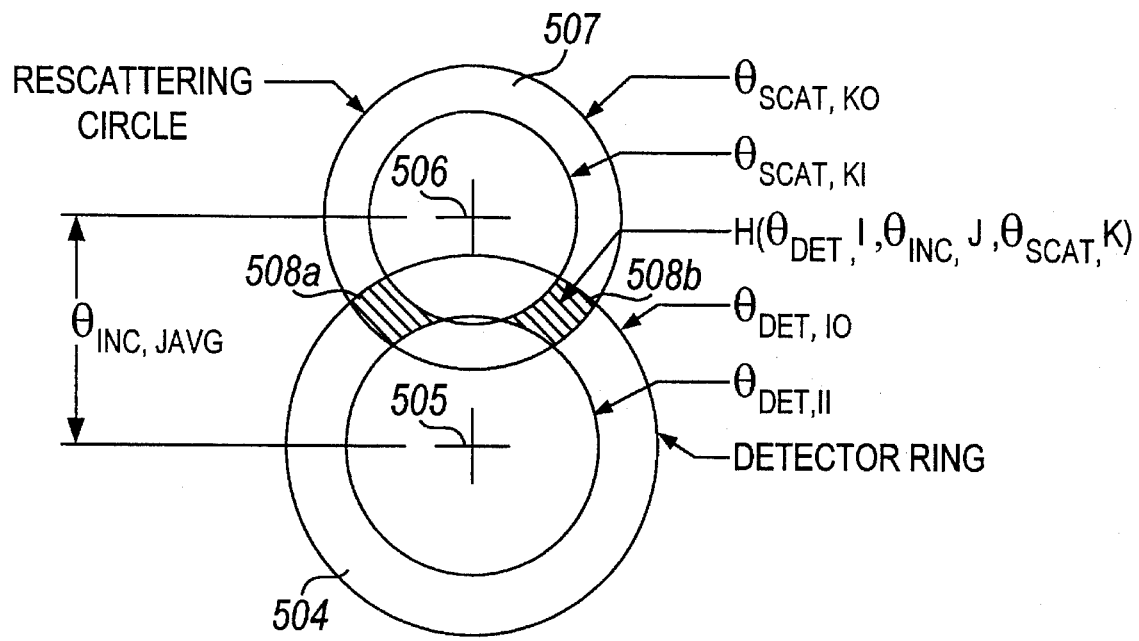
FIG. 5b maps the rescattering geometry to a specific ring i in detector 205.

The redistribution kernel function h is defined with respect to FIGS. 5a and 5b. FIG. 5a shows the definitions of various angles in the rescattering geometry. FIG. 5b maps the rescattering geometry to a specific ring i in detector 205 of ELD instrument 200. As shown in FIG. 5a, an incident ray 501 propagating at an angle $\theta_{inc}$ from the optical axis of ELD instrument 200 is scattered as rescattered ray 503 at an angle $\theta_{scat}$. In FIG. 5b, which is a view in the plane of detector 205, detector ring 504 represents the detector ring i on which rescattered ray 503 would impinge, if no further scattering occurs. Point 505 represents the optical axis of ELD instrument 200. Thus, without the rescattering, incident ray 506 would impinge at detector 205 on point 506. (Point 506 is, of course, a point on detector ring j). As a result of the rescattering at angle $\theta_{scat,k}$, which represents a discretization of a range j of scattering angles covered by rescattering ring 507, rescattered ray 503 impinge on detector ring i. The redistribution kernel function h is defined as the overlapping areas 508a and 508b of detector ring 504 and rescattering ring 507, normalized to the area of rescattering ring 507.

A scattering signature $S_n(\theta)$ can be defined as the scattering signature for exactly n scattering events. Under such definition, $S_n(\theta)$ is given by:

$$S_n(\theta) = H S_{n-1}(\theta)$$

The probability of scattering at angle $\theta_{scat,k}$, i.e. $P_{scat}(\theta_{scat,k})$, is then $S_1(\theta)$. The measured light intensity distribution, or measured multiple scattering signature, $S_m(\theta)$, is then given by:

$$S_m = \sum_{n=1}^{\infty} P_n * S_n = \sum_{n=1}^{\infty} (P_n * H^{n-1}) S_1$$

Since H is also a function of $S_1(\theta)$, $S_1$ cannot be solved using linear algebra. The present invention provides an iterative method to allow $S_1$ to be solved numerically. This method is illustrated by way of example in the flow diagram 600 of FIG. 6. Flow diagram 600 is an example, for this application, of a numerical method similar to the Newton's method. Of course, within the scope of the present invention, other numerical methods can also be used.

Figure 6:
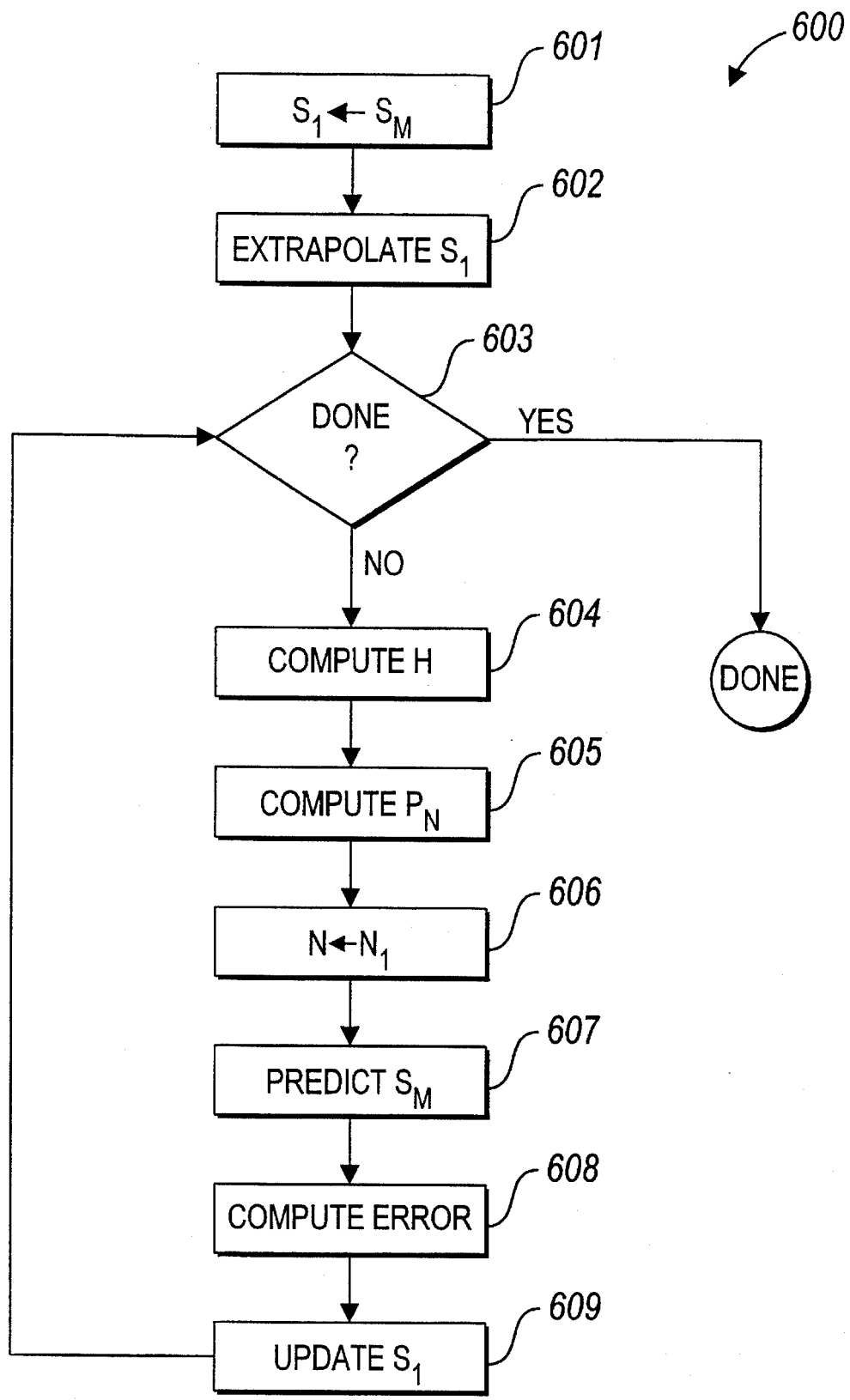
FIG. 6 is a flow diagram 600 illustrating an iterative numerical method for solving the single scattering signature $S_1$.

As shown in FIG. 6, at step 601, an initial prediction of the single scattering signature $S_1$ is provided by the measured multiple scattering signature $S_m$. In the present embodiment, detector 205 of ELD instrument 200 does not detect large scattering angles. The scattered light intensities at these larger scattering angles are estimated from the measured scattering signature $S_m$, at step 602. At decision step 603, which is revisited at every iteration, termination conditions are evaluated. In this embodiment, at step 603, the method of flow diagram 600 terminates when: (i) an updated error variable $\chi^2$ is less than a predetermined value $\epsilon_1$, (ii) the updated error variable $\chi^2$ differs from its previous value by a predetermined value $\epsilon_2$, or (iii) step 603 has been carried out for more than a predetermined number of times $\psi$. In this embodiment, both $\epsilon_1$ and $\epsilon_2$ are both set to $1.0e^{-8}$ and $\psi$ is set to 100.

If none of the termination conditions at step 603 is met, at step 604, the updated transfer function H is computed using the current value of single scattering signature $S_1$. Thus, the following computation is performed:

$$H(i,j) = \sum_k h(i,j,k) S_{1,k}$$

where $S_{1,k}$ is the value of $S_1$ at the discretized scattering angle k. At step 605, the probabilities of various multiple scattering, i.e. $P_n$, are computed. In this embodiment, initially, probabilities of nine scattering modes are computed (i.e. n is set from 1 to 9). To minimize computation, each $P_n$ is compared to $P_1$. If $$\frac{P_{n_1}}{P_1}$$

is less than a predetermined value $\epsilon_3$, for $n_1 > 1$, the contribution to multiple scattering signature $S_m$ by the multiple scattering modes above $n_1$ scattering events is assumed to be negligible. In this embodiment, $\epsilon_3$ is set to 0.005. Thus, at step 606, if $$\frac{P_{n_1}}{P_1} \leq \epsilon_3,$$

n is set to $n_1$. A predicted multiple scattering signature $S_{mp}$ is then computed at step 607, using the iterative procedure:

$$S_{mp} \leftarrow P_n S_{temp}; \quad S_{temp} \leftarrow H S_{temp}$$

for n running between 2 and $n_1$, where $S_{temp}$ is a temporary variable holding the value of $H^{n-i} S_1$. At the beginning of step 607, both $S_{mp}$ and $S_{temp}$ are assigned the value $S_1$. Using this iterative procedure, successive $H_n$'s are each obtained by a single matrix multiplication step, multiplying $H^{n-1}$, i.e. the immediately previous value of $S_{temp}$ already computed, to H.

Having computed the predicted multiple scattering signature $S_{mp}$, the error variable $\chi^2$ is updated, at step 608, by:

$$\chi^2 \leftarrow \sum_i (S_{mp} - S_m)^2$$

over the discretized angles i of scattering. At step 609, the value of $S_1$ is updated using the relation:

$$S_1 \leftarrow \left(\frac{S_m}{S_{mp}}\right) S_1$$

The method then returns to step 603 to determine if any of the termination conditions is met.

The method of the present invention have been applied successfully to measurements involving particles of aluminum oxide. The results of these measurements are summarized in FIGS. 7 and 8.

Figure 7:
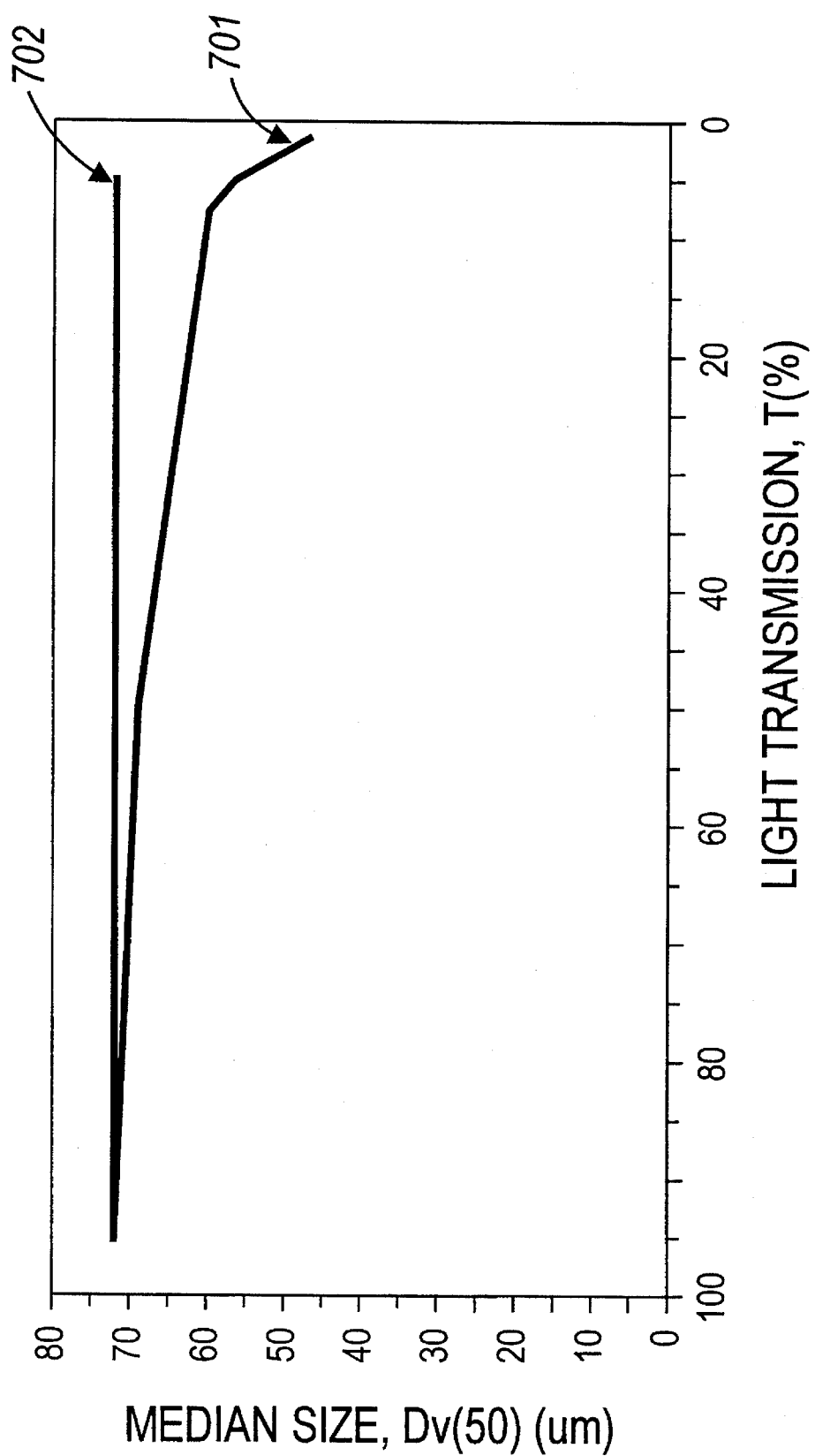
FIG. 7 shows the median particle sizes ($D_v(50)$) measured, with and without applying the multiple scattering correction of the present invention, under various light transmission conditions.

FIG. 7 shows the median particle sizes ($D_v(50)$) measured, with and without applying the multiple scattering correction of the present invention, under various light transmission conditions. As shown in FIG. 7, curve 701 is the median particle sizes measured, without applying the multiple scattering correction of the present invention, between 1% light transmission, an optically dense condition (i.e. a high loading condition), and 95% light transmission, an optically clear condition. Curve 702 is the median particles sizes measured, with application of the multiple scattering correction of the present invention, between 5% light transmission and 95% light transmission. Curve 701 shows that, as transmission decreases to below 70%, i.e. as more and more particles are introduced into the measurement volume, the error in the measured median particle size increases. At 1% transmission, the error is shown to be as large as 40%. On the other hand, as shown in curve 702, with the multiple scattering correction of the present invention applied, the measured median particle size is substantially constant, down to as low as 5% transmission.

Figure 8:
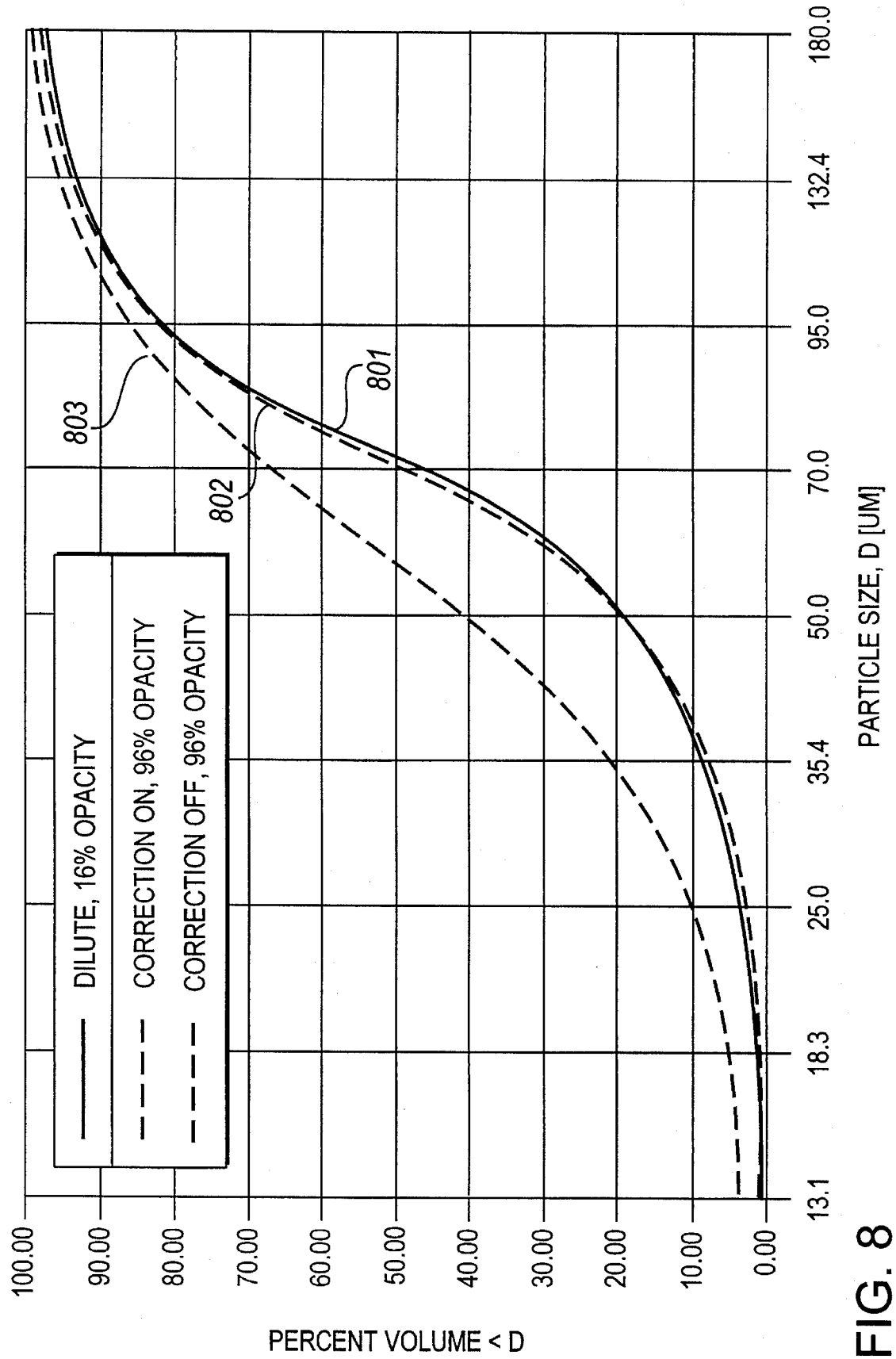
FIG. 8 shows the cumulative particle size distributions measured with and without applying the multiple scattering correction of the present invention.

FIG. 8 shows the cumulative particle size distributions[2] measured with and without applying the multiple scattering correction of the present invention. Curve 801 shows the cumulative particle size distribution measured for a measurement volume having 16% opacity (i.e. 84% transmission). Since this measurement volume is relatively optically clear, the cumulative particle size measured can be used as control for comparing the cumulative particle size distributions measured under a high loading condition, with and without the multiple scattering correction of the present invention. Curve 803 is the cumulative particle size distribution measured, for a 96% opacity (i.e. 4% transmission) measurement volume, without the multiple scattering correction of the present invention. As seen in FIG. 8, curve 803 deviates from curve 801 substantially and essentially overcounting particles at the smaller particle sizes. Curve 802 is the cumulative particle size distribution measured in a measurement volume having a 96% opacity using the multiple scattering correction of the present invention. Curve 802 is shown tracking the control curve 801 almost perfectly. Thus, FIGS. 7 and 8 clearly demonstrate the effectiveness of the multiple correction of the present invention under high loading conditions.

[2] A cumulative particle size distribution shows the percentage by volume of particles (y-axis) having a diameter less than a given value (x-axis).

An example of a computer program which applies the present invention to obtain a single scattering signature from a measured scattering signature is provided in the listing of computer programs attached hereto as Appendix A. This example is written in the C++ programming language well-known to those of ordinary skill in the art.

The above detailed description is provided to illustrate specific embodiments of the present invention and is not intended to be limiting. Numerous variations and modifications within the scope of the present invention are possible. The present invention is defined by the appended claims hereinbelow.

We claim:

1. In an ensemble laser diffraction instrument, a method for providing a single scattering signature from a measured scattering signature, said single scattering signature being applicable to accurately computing a particle size distribution, said method comprising the steps of:

measuring a scattering signature $S_m$;

assigning an initial value as a current value for a single scattering signature $S_1$; and Using said current value, iteratively performing, until a predetermined convergence criterion is met, the steps of:
   (a) computing a current value of a scattering redistribution function H using said current value of said single scattering signature $S_1$;
   (b) computing a pluralities of probability of multiple scattering $P_n$, each of said $P_n$ denoting the probability of exactly n scattering events, n being an integer greater or equal to 1;
   (c) computing a predicted multiple scattering signature $S_{mp}$ using the relation:

$$S_{mp} = \sum_{k=1}^{n} P_n H^{n-1} S_1$$

and (d) updating said current value of said single scattering signature $S_1$ using said measured multiple scattering signature $S_m$ and said predicted multiple scattering signature $S_{mp}$.

2. A method as in claim 1, wherein said step of computing said predicted multiple signature $S_{mp}$ is carried out iteratively such that each $H^n$ is obtained by a single matrix multiplication step, multiplying $H^{n-1}$, already computed, to H.

3. A method as in claim 1, wherein said step of updating said current value of said single scattering signature $S_1$ uses the relation:

$$S_1 \leftarrow \left(\frac{S_m}{S_{mp}}\right) S_1.$$

4. A method as in claim 1, wherein said predetermined convergence criterion is met when the mean square error between said predicted multiple scattering signature $S_{mp}$ and said measured multiple scattering signature $S_m$ is less than a predetermined value.

5. A method as in claim 4, wherein said predetermined convergence criterion is met the difference between successive values of said mean square error is less than a second predetermined value.

6. A method as in claim 1, wherein said predetermined convergence criterion is met when said step of iteratively performing is performed a predetermined number of times.

7. A method as in claim 1, further comprising the step of restricting the value n according to relative magnitudes of the probabilities $P_n$ and $P_1$.

8. A method as in claim 1, wherein said initial value of single scattering signature $S_1$ is said measured multiple scattering signature $S_m$.

* * * * *

UNITED STATES PATENT AND TRADEMARK OFFICE
CERTIFICATE OF CORRECTION

PATENT NO. : 5,619,324
DATED : April 8, 1997
INVENTOR(S) : Harvill, Thomas L.; Holve, Donald J.

It is certified that error appears in the above-identified patent and that said Letters Patent is hereby corrected as shown below:

Col. 6, line 63, delete "$H^{n-i}S_1$" and insert --$H^{n-1}S_1$--.

Col. 6, line 65, delete "$H_n$'s" and insert --$H^n$'s--.

Col. 8, line 63, delete "-".

Signed and Sealed this

Fourth Day of November, 1997

BRUCE LEHMAN

*Attest:*

*Attesting Officer*

*Commissioner of Patents and Trademarks*